United States Patent
Kozyuk

(10) Patent No.: US 8,143,460 B2
(45) Date of Patent: *Mar. 27, 2012

(54) APPARATUS AND METHOD FOR INCREASING ALCOHOL YIELD FROM GRAIN

(75) Inventor: Oleg Kozyuk, North Ridgeville, OH (US)

(73) Assignee: Arisdyne Systems, Inc., Cleveland, OH (US)

( * ) Notice: Subject to any disclaimer, the term of this patent is extended or adjusted under 35 U.S.C. 154(b) by 171 days.

This patent is subject to a terminal disclaimer.

(21) Appl. No.: 12/686,549

(22) Filed: Jan. 13, 2010

(65) Prior Publication Data

US 2010/0112125 A1 May 6, 2010

Related U.S. Application Data

(63) Continuation of application No. 12/115,758, filed on May 6, 2008, now Pat. No. 7,667,082.

(60) Provisional application No. 60/917,212, filed on May 10, 2007.

(51) Int. Cl.
C07C 27/00 (2006.01)

(52) U.S. Cl. ........ 568/902; 568/874; 568/903; 568/913; 568/918

(58) Field of Classification Search .......... 568/903, 568/874, 902, 913, 918
See application file for complete search history.

(56) References Cited

U.S. PATENT DOCUMENTS

| | | | |
|---|---|---|---|
| 3,551,073 A | 12/1970 | Petrovits | |
| 3,852,191 A | 12/1974 | Zucker et al. | |
| 3,937,445 A | 2/1976 | Agosta | |
| 4,127,332 A | 11/1978 | Thiruvengadam et al. | |
| 4,217,414 A | 8/1980 | Walon | |
| 4,416,701 A | 11/1983 | Huster et al. | |
| 4,416,989 A | 11/1983 | Kretz | |
| 4,716,218 A | 12/1987 | Chen et al. | |
| 4,810,647 A | 3/1989 | Monceaux et al. | |
| 4,944,163 A | 7/1990 | Niggemann | |
| 5,410,021 A | 4/1995 | Kampen | |
| 5,492,654 A | 2/1996 | Kozyuk et al. | |
| 5,628,623 A | 5/1997 | Skaggs | |
| 5,688,674 A | 11/1997 | Choi et al. | |
| 5,810,052 A | 9/1998 | Kozyuk | |
| 5,810,474 A | 9/1998 | Hidalgo | |
| 5,868,495 A | 2/1999 | Hidalgo | |
| 5,931,771 A | 8/1999 | Kozyuk | |
| 5,937,906 A | 8/1999 | Kozyuk | |
| 5,969,207 A | 10/1999 | Kozyuk | |
| 5,971,601 A | 10/1999 | Kozyuk | |
| 6,012,492 A | 1/2000 | Kozyuk | |
| 6,035,897 A | 3/2000 | Kozyuk | |
| 6,318,649 B1 | 11/2001 | Mazurkiewicz | |
| 6,386,751 B1 | 5/2002 | Wootan et al. | |
| 6,502,979 B1 | 1/2003 | Kozyuk | |
| 6,538,041 B1 | 3/2003 | Marelli | |
| 6,737,099 B2 | 5/2004 | Guraya | |
| 6,802,639 B2 | 10/2004 | Kozyuk | |
| 6,824,086 B1 | 11/2004 | Mazurkiewicz et al. | |
| 6,857,774 B2 | 2/2005 | Kozyuk | |
| 7,086,777 B2 | 8/2006 | Kozyuk | |
| 7,087,178 B2 | 8/2006 | Romanyszyn et al. | |
| 7,101,691 B2 | 9/2006 | Kinley et al. | |
| 7,135,155 B1 | 11/2006 | Long, Jr. et al. | |
| 7,138,257 B2 | 11/2006 | Galli et al. | |
| 7,178,975 B2 | 2/2007 | Kozyuk | |
| 7,207,712 B2 | 4/2007 | Kozyuk | |
| 7,247,244 B2 | 7/2007 | Kozyuk | |
| 7,314,306 B2 | 1/2008 | Kozyuk | |
| 7,452,425 B1 | 11/2008 | Langhauser | |
| 2002/0009414 A1 | 1/2002 | Moser et al. | |
| 2002/0054995 A1 | 5/2002 | Mazurkiewicz | |
| 2003/0026888 A1 | 2/2003 | Guraya | |
| 2004/0028622 A1 | 2/2004 | Gurin | |
| 2004/0187863 A1 | 9/2004 | Langhauser | |
| 2005/0118692 A1 | 6/2005 | Kinley et al. | |
| 2005/0136520 A1 | 6/2005 | Kinley et al. | |
| 2005/0233030 A1 | 10/2005 | Lewis et al. | |
| 2005/0239181 A1 | 10/2005 | Lewis et al. | |
| 2006/0286654 A1 | 12/2006 | Kinley et al. | |
| 2007/0037267 A1 | 2/2007 | Lewis et al. | |
| 2007/0066480 A1 | 3/2007 | Moser et al. | |
| 2007/0152355 A1 | 7/2007 | Hartlely | |
| 2007/0161095 A1 | 7/2007 | Gurin | |
| 2007/0178567 A1 | 8/2007 | Lewis | |
| 2007/0202214 A1 | 8/2007 | Lewis et al. | |
| 2008/0044891 A1 | 2/2008 | Kinely et al. | |
| 2008/0099410 A1 | 5/2008 | Sprague | |
| 2008/0277264 A1 | 11/2008 | Sprague | |
| 2009/0186383 A1 | 7/2009 | Mancosky | |

FOREIGN PATENT DOCUMENTS

| EP | 0 948 400 | 7/2003 |
|---|---|---|
| GB | 2016940 | 9/1979 |
| WO | 2008/140997 A1 | 11/2008 |

OTHER PUBLICATIONS

International Search Report and Written Opinion of the International Searching Authority from corresponding PCT application No. PCT/US08/62746, mailed Aug. 22, 2008. International Search Report and Written Opinion issued Aug. 30, 2011 in PCT Application PCT/US2010/059164.

*Primary Examiner* — Elvis O Price

(74) *Attorney, Agent, or Firm* — Pearne & Gordon LLP

(57) ABSTRACT

A method comprising applying a controlled flow cavitation apparatus to an alcohol production process in order to increase alcohol yield. A grain-based liquid medium comprising grain and a liquid carrier can be passed through a controlled flow cavitation apparatus at a velocity capable of generating a hydrodynamic cavitation zone where the grain size can be reduced. One or more controlled flow cavitation apparatuses can be applied at various points of an alcohol production process, such as a starch-to-ethanol production process.

10 Claims, 4 Drawing Sheets

APPARATUS AND METHOD FOR INCREASING ALCOHOL YIELD FROM GRAIN

This application is a continuation of U.S. patent application Ser. No. 12/115,758 filed May 6, 2008, which claims the benefit of U.S. provisional application Ser. No. 60/917,212 filed May 10, 2007, the contents of which are incorporated herein in their entirety by reference.

FIELD OF THE INVENTION

The present invention relates generally to alcohol production and more particularly to alcohol production using a controlled flow cavitation apparatus.

BACKGROUND OF THE INVENTION

Alcohols are a renewable and clean fuel source. For example, ethanol can be produced in large part from corn by the fermentation of starch. Generally, ethanol production is accomplished through a fermentation and distillation process starting with the release of starches which convert to sugars that yeasts can convert to alcohol. At an industrial level, yeast fermentation converts about one-third of the corn into ethanol. Improving the yield of ethanol from corn can increase the amount of ethanol produced and lower the amount of corn needed for ethanol production.

Ethanol production facilities often begin the production process with a dry or wet milling process, which can consume much energy and require cleanup or recovery of chemicals. In dry milling, corn is ground up by a hammer or roller mill into a manageable mixture of coarse particles. The dry mixture is combined with water and enzymes such that the starch breaks up into small sections that can be subjected to a saccharification phase and further fermented with yeast to convert the sugars to ethanol. The yield of ethanol from the ground-up corn can only be as high as the total starch content of the corn and the availability of that starch to the enzymes used in the saccharification process. Commercial ethanol plants do not achieve maximum theoretical ethanol yields.

Accordingly, there is a need in the art for an apparatus and method for increasing ethanol yield from corn. The method preferably is low energy and minimizes use of processing chemicals. Further, it is also desirable that the apparatus and method increase the efficacy of enzymes in order to improve starch and sugar release.

SUMMARY OF THE INVENTION

A method of producing alcohol from grain comprising providing a grain-based liquid medium comprising grain and a liquid carrier, wherein the grain-based liquid medium is forced through a controlled flow cavitation apparatus at a velocity or processing pressure capable of generating a hydrodynamic cavitation zone. The grain-based liquid medium is maintained in the hydrodynamic cavitation zone for less than 1 second.

A method of increasing ethanol yield in a starch-to-ethanol production process comprising passing a grain-based liquid medium through a controlled flow cavitation apparatus prior to a distillation phase of the process. The average grain size in the grain-based liquid medium is reduced at least 5 percent after being passed through the controlled flow cavitation apparatus. The average grain size reduction is based on the average grain size in the grain-based liquid medium prior to passing through the controlled flow cavitation apparatus.

A method of increasing ethanol yield in a starch-to-ethanol production process comprising passing a grain-based liquid medium processing stream at one or more points of an ethanol production process through a controlled flow cavitation apparatus. The controlled flow cavitation apparatus reduces the amount of residual starch remaining in the ethanol production process prior to a distillation phase.

BRIEF DESCRIPTION OF THE DRAWINGS

Aspects of the invention will be appreciated by a person having ordinary skill in the art based on the following description with reference to the following drawings, which are provided by way of illustration and not limitation.

DETAILED DESCRIPTION OF PREFERRED EMBODIMENTS

Herein, when a range such as 5-25 (or 5 to 25) is given, this means preferably at least 5 and, separately and independently, preferably not more than 25.

Figure 1:
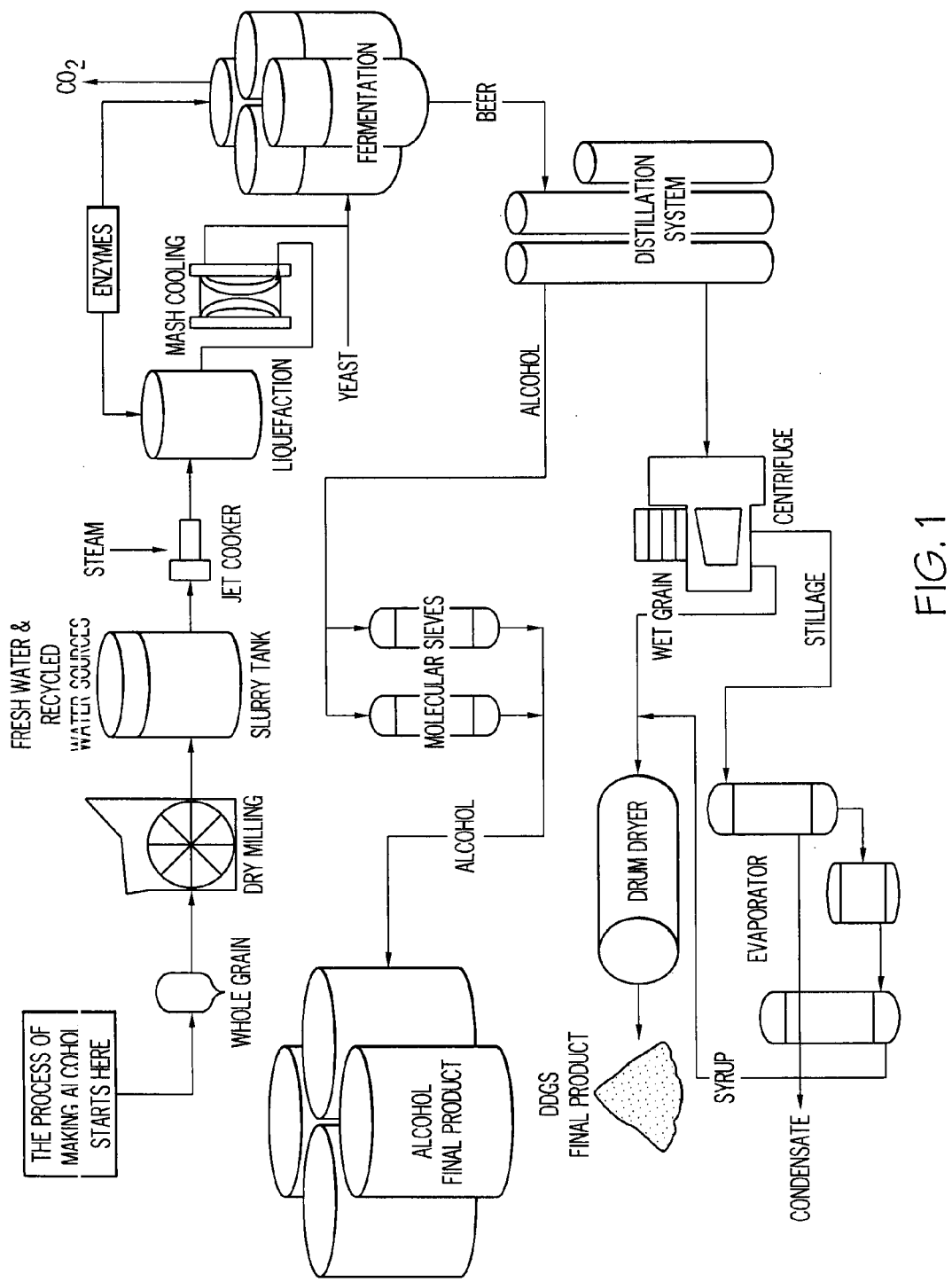
FIG. 1. is a schematic of an alcohol production process.

FIG. 1 shows an alcohol production process, such as that used to produce ethanol, for example, a starch-to-ethanol production process. The alcohol production process shown utilizes a milling phase, such as a dry milling step, to grind grain, such as whole kernel corn, into meal or powder. Preferably, the grain is screened to remove foreign material or debris, such as dirt, stalks, leaves and the like. Although corn is shown as the whole grain in FIG. 1, any grain can be used. For example, grains can include corn, rye, sorghum, wheat, beans, barley, oats, rice, or combinations thereof. As used herein, the term "grain" can comprise a whole grain or portions or particles of a whole grains such as the product from a dry- or wet-milling process used in an alcohol production process. The ground grain powder is combined with a fluid carrier, such as water, to make a grain-based liquid medium, which can be in the form of a slurry. The grain-based liquid medium or grain-based liquid medium processing stream comprises preferably at least 5, 10, 15, 20, 25, 30, 40, 50 or 60 weight percent grain, based on the total weight of the liquid medium. As shown in FIG. 1, the grain-based liquid medium comprises corn grains and a liquid carrier, such as water.

The grain-based liquid medium is then heated in a cooking phase, such as by a jet cooker, at approximately 200° F. or above at 10 to 40 psi. The grain-based liquid medium is subsequently held at an elevated temperature of about 180° to 195° F. for a period of about 4 to 8 hours. Alternatively, the temperatures, pressures and time periods above can vary widely depending the specific application. The jet cooker and the subsequent heating period preferably solubilize the starch contained the in grains.

In the alcohol production process, a liquefaction phase follows the cooking phase, at which point alpha enzymes are added to the grain-based liquid medium in order to break down the starch polymer into short sections. The short sections can be maltodextrins and oligosaccharides. The liquefaction phase is followed by a saccharification phase in which enzyme gluco amylase is added to the medium. The enzymes in the saccharification phase create a sugar mash that can be transferred into fermentation tanks where yeast can convert the sugars into carbon dioxide and alcohol, such as ethanol. The fermentation product can also contain soluble and insoluble solids, i.e. non-fermentable components, left over from the grain. A distillation phase following the fermentation phase separates the liquid carrier, usually water, ethanol, and whole stillage. The water can be recycled and used, for example, in the slurry tanks. The non-fermentable compounds are further separated in the distillation process, and can also be sold as high-protein animal feed.

Commercial alcohol or ethanol plants do not yield the maximum conversion of starch to alcohol. In part, it is believed that maximum alcohol yields are not achieved because enzymes used to convert starch to sugar have difficulty accessing all of the starch contained in the grains. Starch in the grains binds to proteins, fiber, amyloplasts, and the like, which decreases the effectiveness of the cooking and heating steps to break down and gelatinize the starch. Further, starch has an internal molecular composition that makes it difficult to break the starch in the grains into smaller sections such that the enzymes can easily access the starch and convert it into sugar that can be fermented into alcohol. In order to improve conversion into ethanol of the starches contained in the grains, the grains can be processed to render the starches to be more accessible to the enzymes. One method of making the starches more accessible to the enzymes is to reduce the particle size of the grains after dry- or wet-milling processes used in conventional alcohol production processes.

A controlled flow cavitation apparatus can be integrated into an alcohol production process, preferably before a distillation phase, to reduce the particle size of grain in a grain-based liquid medium such that the surface area and accessibility of the starches contained in the grains increases. The use of a controlled flow cavitation apparatus can reduce the amount of residual starch remaining in said ethanol production process prior to distillation because more starch is, accessible and therefore converted into sugar. Further, controlled flow cavitation can promote the stripping away of cell macromolecules such as protein and fiber from the surface of starch granules, as well as the opening or breaking of gelatinized starch granules, all of which make starch granules more accessible and available to enzymes during liquefaction and saccharification. Controlled flow cavitation applied during liquefaction in an alcohol process according to the present invention allows hydrolyzation or depolymerization of long polymeric macromolecules such as starch, protein, and, at very high power levels, nucleic acids and will increase the rate of liquefaction and saccharification of the starch by making the components more accessible to alpha-amylase and glucoamylase, the normal active enzymes used in liquefaction and saccharification. Thus, use of a controlled flow cavitation apparatus has multiple benefits, such as an efficiency increase of alcohol production, accelerated particle size reduction and consistency with lower energy consumption during milling, enhanced efficacy of enzymes and improved starch and sugar release during hydrolysis, liquefaction and/or saccharification.

Use of a controlled flow cavitation apparatus at one or more various points of an alcohol production process can improve alcohol yields. One strategy to improve alcohol production can be to integrate a controlled flow cavitation apparatus into existing dry- or wet-milling alcohol plants prior to or during liquefaction. In another embodiment, a controlled flow cavitation apparatus can be retrofitted or integrated in a slurry tank and/or liquefaction tank. In another embodiment, a controlled flow cavitation apparatus can be applied after whole grain milling and before cooking or heating of starch in the slurry tank.

Figure 2:
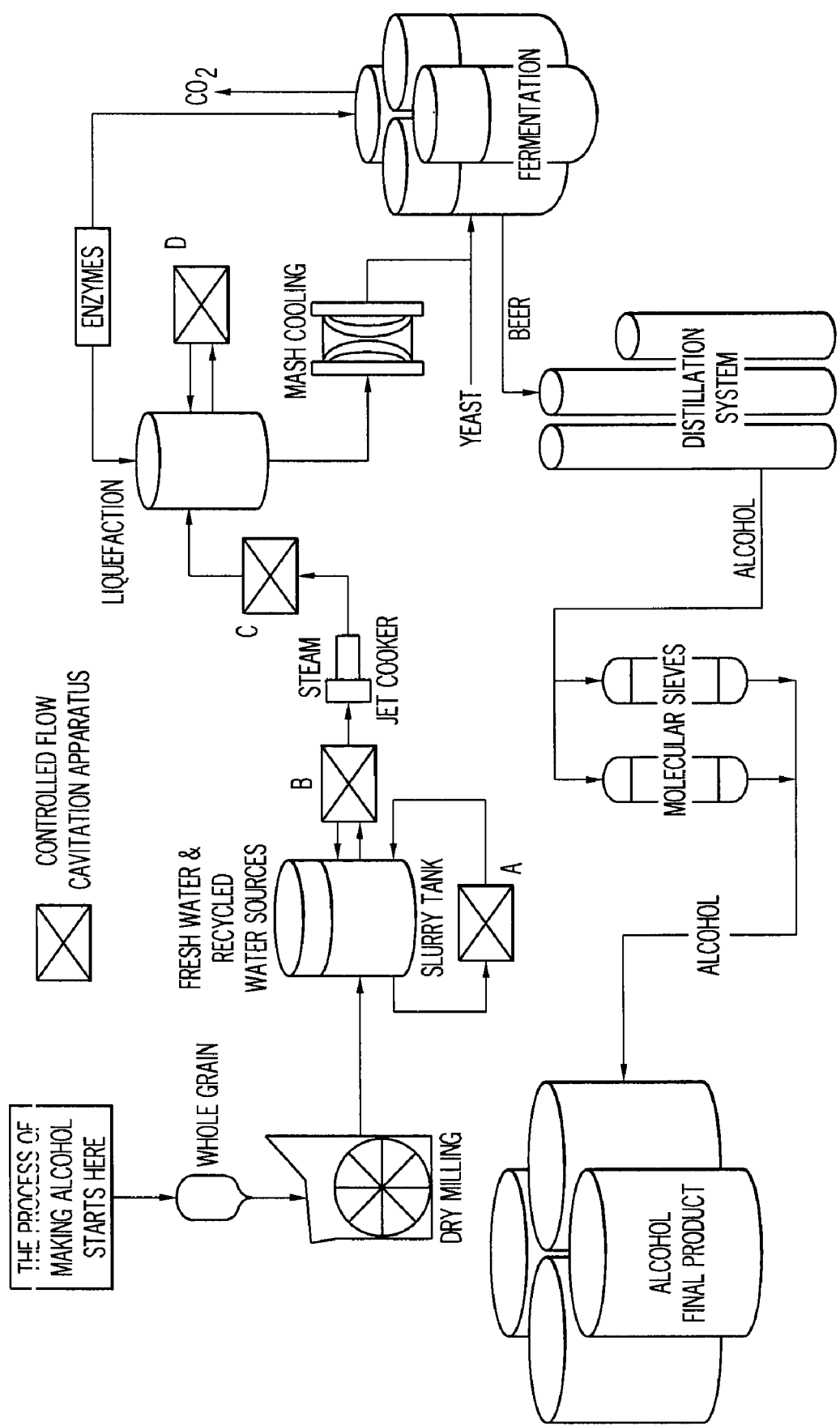
FIG. 2 is a schematic of an alcohol production process. Locations A through D represents process phases in which a controlled flow cavitation apparatus can be used.

FIG. 2 illustrates four points, A through D, at which a controlled flow cavitation apparatus can be integrated or retrofitted into a conventional alcohol production process. Generally, points A and B illustrate a controlled flow cavitation apparatus positioned before a cooking phase of an alcohol production process, whereas points C and D illustrate a controlled flow cavitation apparatus positioned after the cooking phase.

Point A illustrates a controlled flow cavitation apparatus integrated with a slurry tank, which contents can include grain, such as corn grains, and a liquid carrier such as water. As shown, the controlled flow cavitation apparatus is positioned in a fluid circulation loop that is connected to the slurry tank such that the grain-based liquid medium in the slurry tank can be circulated through the controlled flow cavitation apparatus as many times as desired in order to reduce the particle size of the grains in the slurry tank. Any means can be used to circulate the grain-based liquid medium through the controlled flow cavitation apparatus, such as a pump. Point B illustrates a controlled flow cavitation apparatus positioned downstream of a slurry tank as described above and upstream of a cooker, which is shown as a jet cooker. Point B further illustrates that the controlled flow cavitation apparatus can be in a recirculation loop with the slurry tank. In this configuration, the grain-based liquid medium can be circulated through the controlled flow cavitation apparatus multiple times before the stream is sent to the cooker. Point C illustrates a controlled flow cavitation apparatus positioned between the cooking phase and the liquefaction phase of an alcohol production process. Point D illustrates a controlled flow cavitation apparatus integrated with a liquefaction tank, which contents can include grain, such as corn grains, and a liquid carrier such as water. As shown, the controlled flow cavitation apparatus is in a fluid circulation loop that is connected to the liquefaction tank such that the grain-based liquid medium in the liquefaction tank can be circulated through the controlled flow cavitation apparatus as many times as desired in order to reduce the particle size of the grains in the liquefaction tank. Any means can be used to circulate the grain-based liquid medium through the controlled flow cavitation apparatus, such as a pump. The controlled flow cavitation apparatus access points, A through D, discussed above are only a few points where an apparatus can be positioned in an alcohol production process. In another embodiment, multiple controlled flow cavitation apparatuses can be located at one or at all of the points shown in FIG. 2.

The invention can be practiced by using any of the known controlled flow cavitation apparatuses, such as those described in U.S. Pat. Nos. 5,810,052; 5,931,771; 5,937,906; 5,971,601; 6,012,492; 6,502,979; 6,802,639; and 6,857,774, the entire contents of which are incorporated herein by reference. Some preferred embodiments of controlled flow cavitation apparatuses are described below and shown in FIGS. 3 and 4. Application of one or more controlled flow cavitation apparatuses to one or more various processing points in an alcohol production process can be integrated with minimal retrofitting of tanks or piping. At one or more points in an alcohol production process, the controlled flow cavitation apparatuses can be used individually, in series or in parallel, depending on the magnitude of grain size reduction that is desired. It is believed that alcohol yield can be increased at least 2 to 5 percent with the use of a controlled flow cavitation apparatus as described herein.

Figure 3:
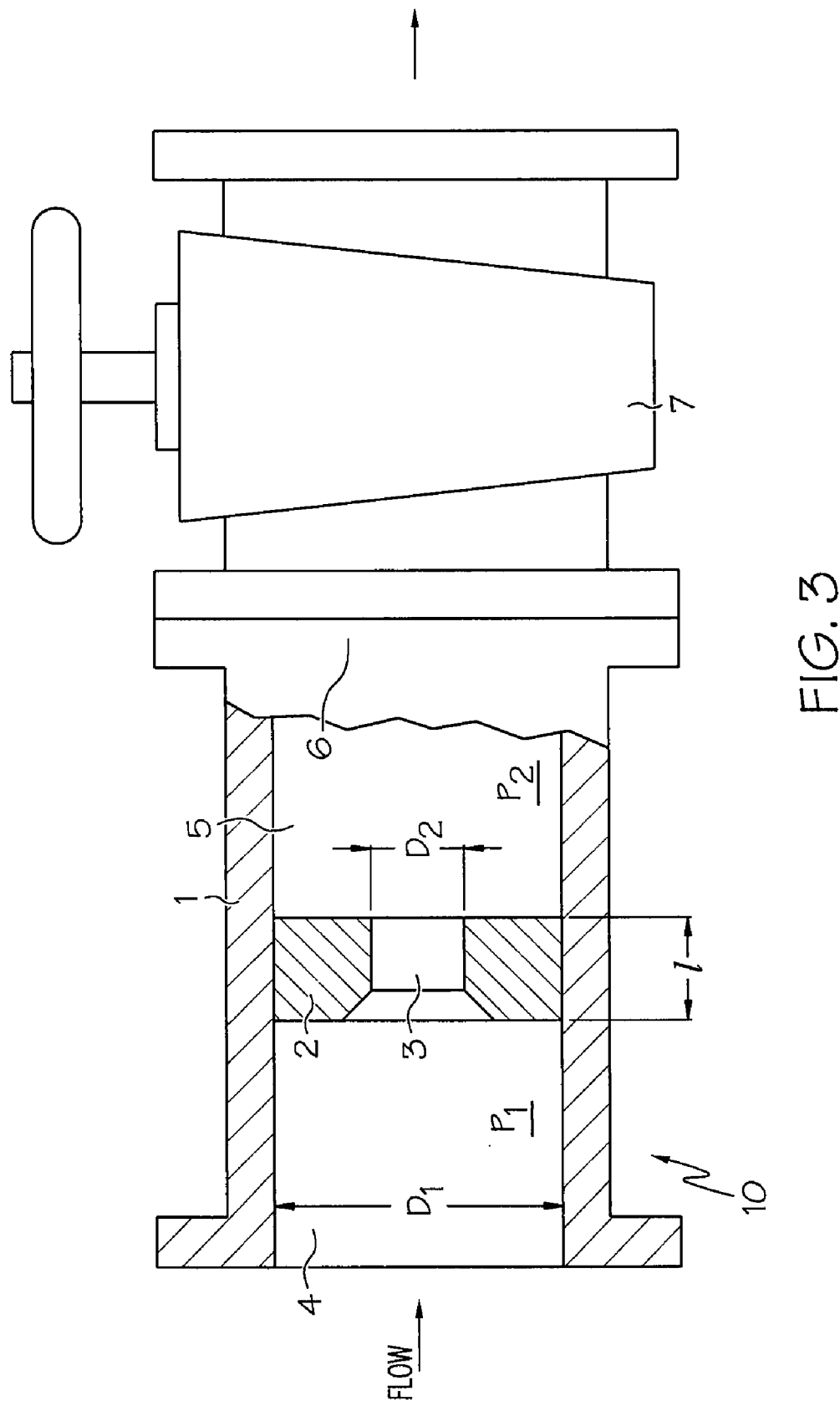
FIG. 3 is a cross section view of a controlled flow cavitation apparatus according to an embodiment of the invention.

FIG. 3 provides a cross section view of one embodiment of the present invention in which a controlled flow cavitation apparatus 10 can process a grain-based liquid medium. The controlled flow cavitation apparatus 10 comprises a flow-through channel 1 comprising a first chamber 4 and a second chamber 5. The first chamber 4 and second chamber 5 of the flow-through channel 1 are divided by a localized flow constriction 2. The first chamber 4 is positioned upstream of the localized flow constriction 2 and the second chamber 5 is positioned downstream of the localized flow constriction 2, as viewed in the direction of movement of flow, such as a grain-based liquid medium. Localized flow constriction can be achieved by a diaphragm with one, or more, orifices 3. Although not shown; the flow-through channel can have two or more localized flow constrictions 2 in series. For example, a first localized flow constriction 2 can have one orifice 3 having a first diameter and a second localized flow constriction 2 can have one orifice 3 having a second diameter, wherein the first localized flow constriction is upstream of the second localized flow constriction. The first and second diameters of the in-series orifices 3 can be the same or vary, such as the first orifice 3 diameter being smaller or larger than the second orifice 3 diameter.

As shown in FIG. 3, the controlled flow cavitation apparatus 10 comprises one cylindrical orifice 3. The orifice 3 of the apparatus 10 can be any shape, for example, cylindrical, conical, oval, right-angled, square, etc. Depending on the shape of the orifice 3, this determines the shape of the cavitation jets flowing from the localized flow constriction 2. The orifice 3 can have any diameter, $D_2$, for example, the diameter can be in the range of about 0.1 to 10 mm, and preferably less than 10 mm, more preferably less than 5 mm and more preferably less than 3 mm. In one example, the orifice 3 diameter can be about 3 mm or about 4 mm. Alternatively, the orifice 3 can have a diameter greater than 10 mm.

At outlet 6 from the second chamber 5, a localized hydraulic resistance 7 can be used to maintain back pressure in the flow-through channel 1, the first chamber 4 or second chamber 5. The localized hydraulic resistance 7 can be valve as known in the art, such as a ball valve, butterfly valve, needle valve or gate valve. As shown, the first chamber 4 has a pressure $P_1$ and the second chamber 5 has a pressure $P_2$. Flow into the apparatus 10 can be provided with the aid of fluid pumping devices as known in the art, such as a pump, centrifugal pump, positive-displacement pump or diaphragm pump. An auxiliary pump can provide flow under a static pressure $P_1$ to the first chamber 4. As discussed herein, pressure $P_1$ is defined as the processing pressure for the controlled flow cavitation apparatus 10. The processing pressure is preferably at least 30, 40, 50, 60, 70, 80, 90, 100, 120, 140, 150, 170, 200, 300, 400, 500, 600, 700, 800, 850, 900, or 1000, psi. The processing pressure is reduced as the grain-based liquid medium passes through the flow-through channel 1 and orifice 3. Maintaining a pressure differential across the orifice 3 allows control of the cavitation intensity in the flow through channel 1. The pressure differential across the orifice 3 is preferably at least 30, 40, 50, 60, 70, 80, 90, 100, 120, 140, 150, 170, 200, 300, 400, 500, 600, 700, 800, 850, 900, or 1000, psi. The velocity of the grain-based liquid medium through the one or more orifices 3 in the controlled flow cavitation apparatus is preferably at least 1, 5, 10, 15, 20, 25, 30, 40, 50, 60 or 70 meters per second (m/s).

In the examples below, the controlled flow cavitation apparatus 10 described herein can be used as a single-pass grain size reducer or, alternatively, multiple controlled flow cavitation apparatuses 10 can be used in series or in parallel to reduce grain size as desired. For instance, as described in the examples below, a controlled flow apparatus can optionally have one or more localized flow constrictions that can reduce grain size in a staged manner. In other words, the grain size in a processing stream can be partially reduced in a first hydrodynamic cavitation zone locally at a first localized flow constriction and then further reduced in a second hydrodynamic cavitation zone locally at a second localized flow constriction.

The flow through the controlled flow cavitation apparatus 10 can be collected in a tank, such as a slurry tank or liquefaction tank. If desired, the collected flow having grains of reduced size can be re-circulated through the controlled flow cavitation apparatus one or multiple times in order to further mix the grain-based liquid medium and/or reduce the grain size. In other words, a grain-based fluid medium can be passed through a controlled flow cavitation apparatus a number of time until the desired grain size reduction is achieved. For example, the grain-based liquid medium can be circulated through a controlled flow cavitation apparatus 10 at least 1, 2, 3, 4, 5, 7, 9, 10, 12, 14, 15, 20, 25, 30, 40, 50, 60, 70, 80, 90, or 100, times. The grain-based liquid medium is preferably circulated through a controlled flow cavitation apparatus 10 a number of times, or otherwise processed at a speed or pressure, sufficient to reduce the average diameter of the grain (grain size) contained in the grain-based liquid medium at least 5, 10, 20, 30, 40, 50, 60, 70 or 80 percent, based on the original average diameter of the grain in the grain-based liquid medium before being passed through the controlled flow cavitation apparatus.

The orifice 3 or orifices (not shown) create a hydrodynamic cavitation zone that promote a high density of cavitation power dissipation locally inside the flow-through channel 1, and more preferably in the orifice 3 chamber and downstream of the orifice 3 in the second chamber 5. The high energy dissipation in the hydrodynamic cavitation zone causes the grains in the grain-based liquid medium to be broken up such the particle size or average diameter of the grains is reduced. The size of the of the grains in the grain-based liquid medium is preferably reduced at least 1, 3, 5, 7.5, 10, 15, 20, 25, 30, 40, 50, 60, 70 or 80 percent, based on the average grain size in the brain-based liquid medium. The grain size can be measured as is known in the art, such as using a microscope for microscopic examination. As used herein, grain size refers to the average diameter of the grains in the grain-based liquid medium.

Hydrodynamic cavitation arises in the fluid jets flowing from the orifice 3 in the form of intermingling cavitation bubbles and separate cavitation cavities. The length (l) in orifice 3 in localized flow constriction 2 is selected in such a manner in order that the residence time of the cavitation bubble in the orifice 3 and/or the second chamber 5 does not exceed 1 second or preferably 0.1 second. Preferably, the grain-based fluid medium is maintained in the hydrodynamic cavitation zone preferably not more than 0.1 second, preferably less than 0.01 second, preferably less than 0.008 second, preferably less than 0.006 second, preferably less than 0.004 second, alternatively less than 0.001 second. The time in the hydrodynamic cavitation zone that is needed to reduce the grain size (diameter) is much smaller than know methods, such as ultrasonic or acoustic, and thus the controlled flow cavitation apparatus can reduce processing time and costs associated with an alcohol production process. Because processing time directly relates to the amount of alcohol that can be produced, the use of a controlled flow cavitation apparatus can increase the yield of alcohol and reduce the amount of processing time required to produce the alcohol. Hydrodynamic cavitation is more efficient than acoustic cavitation and much more efficient than conventional agitation and/or heating methods. Further, the scale-up of hydrodynamic cavitation apparatuses is relatively easy compared to other methods, which makes it well suited to the processing of dispersions and slurries, such as those present in an alcohol production process.

The given dynamic pressure and residence time of the bubble in the localized flow constriction 2 allows production of cavitation bubbles and cavities in the liquid flow. The cavity sizes are dependent on the magnitude of the dynamic pressure jet as well as the sizes of orifice 3 in the localized flow constriction 2. Increase of the dynamic pressure jet as well as size of orifice 3 leads to the increase in the sizes of cavitation bubbles. Increase of the dynamic pressure of the cavitation fluid jet also promotes increase of the concentration of cavitation bubbles. Therefore, given the dynamic pressure of the cavitation fluid jet, its shape, and the number of fluid jets, it is possible to produce a cavitation field or zone of cavitation bubbles and their required concentration and sizes. Cavitation bubbles and cavities together with the liquid jets enter into the second chamber 5, where they collapse under the influence of static pressure $P_2$. The energy emitted during collapse of cavitation bubbles is directly proportional to the magnitude of the static pressure in the surrounding liquid bubbles. Therefore, the greater the magnitude of $P_2$ the greater the energy emitted during collapse of cavitation bubbles and the better the dispersion and/or size reduction effect. In other words, the level of energy dissipation in the grain-based fluid medium increases as the magnitude of $P_2$ increases and thus the severity or hardness of collapse of each cavitation bubble separately increases, as well as the level of energy dissipation due to the decrease of the volume in which these bubbles collapse.

As discussed above, the magnitude of static pressure $P_2$ in second chamber 5 is maintained due to the location of the additional localized restriction 7 at the outlet from this chamber. The additional localized restriction may be adjustable or non-adjustable. By utilizing the adjustable additional localized resistance 7 it is possible to control the severity or hardness of cavitation influence and in the same process, the cavitation dispersion and grain size reduction. Such adjustment is more expedient in apparatuses that are intended for dispersing various mediums.

Figure 4:
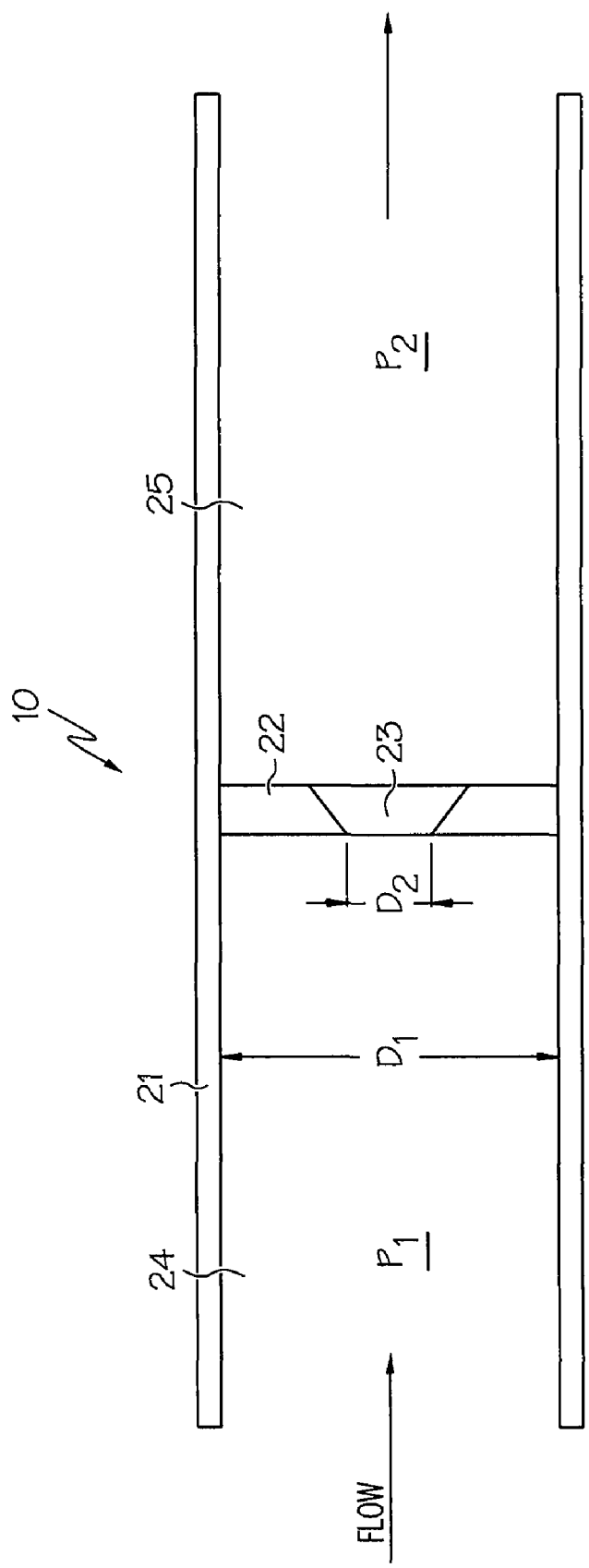
FIG. 4 is a cross section view of a controlled flow cavitation apparatus according to an embodiment of the invention.

In another embodiment, FIG. 4 illustrates a controlled flow cavitation apparatus 10, wherein the sharp-edged orifice 23, positioned in the localized flow constriction 22, has a diameter, $D_2$. Diameter $D_2$ can be in the range of 0.1 to 10 mm as described above, and preferably less than 10 mm. The inlet diameter to the controlled flow cavitation apparatus 10 is designated as $D_1$. Diameter $D_1$ can be 0.25 to 8 inches. The localized flow constriction 22 divides the flow through channel 21 into two chambers, a first chamber 24 having pressure $P_1$ and a second chamber 25 having pressure $P_2$. Although not shown, the controlled flow cavitation apparatus 10 of FIG. 4 can have an additional localized restriction, such as a valve, at the outlet of the second chamber 25 in order to alter the cavitation influence on the dispersion and grain size reduction. The additional localized restriction may be adjustable or non-adjustable. As described above, a grain-based liquid medium can be forced or passed through the controlled flow cavitation apparatus 10 of FIG. 4 in order to reduce the grain size (diameter) of the grains contained in the liquid medium.

In order to promote a further understanding of the invention, the following examples are provided. These examples are shown by way of illustration and not limitation.

Example 1

Two slurries were prepared of 20 weight percent corn mash and 80 weight percent water. The first slurry had an average corn particle size of 242 microns (control diameter). The second slurry had an average corn particle size of 201 microns (control diameter). The corn particle size was measured using microscopic examination and a light scattering technique (Malvern Mastersizer). Both slurries were fed through a controlled flow cavitation apparatus by a pump. The first slurry was passed through a controlled flow cavitation apparatus having two localized flow constrictions in series. The first localized flow constriction contained an orifice having a diameter of 0.048 inch and the second localized flow constriction contained an orifice having a diameter of 0.09 inch. The first slurry had a processing pressure of 70 psi. The pressure differential across the first orifice was about 45 psi and the pressure differential across the second orifice was about 20 psi. The velocity through the first orifice was about 18 m/s. The velocity through the second orifice was about 12 m/s.

Table 1 shows the results of the first slurry experiment.

TABLE 1

| Processing Pressure (psi) | Number of Passes | Duration in the cavitation zone (seconds/pass) | Average particle size (diameter) D43 (μm) |
|---|---|---|---|
| Control | 0 | 0 | 242 |
| 70 | 1 | 0.0060 | 224 |
| 70 | 74 | 0.0060 | 158 |

As can be seen in Table 1, the average corn particle size was reduced after one pass at a processing pressure of 70 psi to 224 microns, or about 7.5 percent of the control diameter. After 74 passes through the controlled flow cavitation apparatus at a processing pressure of 70 psi, the average corn particle size was reduced to 158 microns, or about 35 percent of the control diameter.

The second slurry was passed through a controlled flow cavitation apparatus at a variety of processing pressures. In one case, the second slurry was passed through a controlled flow cavitation apparatus having a localized flow constriction with one orifice having a diameter of 0.048 inch at a processing pressure of 200 psi. The pressure differential across the orifice was about 195 psi. The velocity through the orifice was about 19 m/s. In another case, the second slurry was passed through a controlled flow cavitation apparatus having two localized flow constrictions in series. The first localized flow constriction contained an orifice having a diameter of 0.048 inch and the second localized flow constriction contained an orifice having a diameter of 0.09 inch. The first slurry had a processing pressure of 850 psi. The pressure differential across the first orifice was about 405 psi and the pressure differential across the second orifice was about 220 psi. The velocity through the first orifice was about 55 m/s. The velocity through the second orifice was about 40 m/s. In yet another case, the second slurry was passed through a controlled flow cavitation apparatus having two localized flow constrictions in series. The first localized flow constriction contained an orifice having a diameter of 0.048 inch and the second localized flow constriction contained an orifice having a diameter of 0.09 inch. The first slurry had a processing pressure of 1000 psi. The pressure differential across the first orifice was about 645 psi and the pressure differential across the second orifice was about 350 psi. The velocity through the first orifice was about 62 m/s. The velocity through the second orifice was about 51 m/s.

Table 2 shows the results of the second slurry experiment.

TABLE 2

| Processing Pressure (psi) | Number of Passes | Duration in the cavitation zone (seconds/pass) | Average particle size (diameter) D43 (μm) |
| --- | --- | --- | --- |
| Control | 0 | 0 | 201 |
| 200 | 36 | 0.0036 | 138 |
| 850 | 15 | 0.00017 | 65 |
| 1000 | 4 | 0.00011 | 47 |

As can be seen in Table 2, the average corn particle size was reduced after 36 passes at a processing temperature of 200 psi to 138 microns, or about 31 percent of the control diameter. After 15 passes through the controlled flow cavitation apparatus at a processing pressure of 850 psi, the average corn particle size was reduced to 65 microns, or about 68 percent of the control diameter. After 4 passes through the controlled flow cavitation apparatus at a processing pressure of 1000 psi, the average corn particle size was reduced to 47 microns, or about 77 percent of the control diameter.

As can be seen above, the grain particle size was dramatically reduced by running a grain-based liquid medium through a controlled flow cavitation apparatus as described herein. These results were both surprising and unexpected. It was also surprising and unexpected that the grain particle size was significantly reduced in such a short amount of time, which is a substantial improvement over existing technologies such as ultrasonic.

After grains are reduced in size, they can be run through an alcohol production process as described herein. The reduced grain size promotes higher starch accessibility for the enzymes, such as alpha-amylase and gluco-amylase, and, increases the rate of liquefaction and saccharification of the starch, all of which can result in higher alcohol yields for a given weight of grain. As a result, more alcohol can be produced from a fixed weight of grain being run through an alcohol production process.

The controlled flow cavitation apparatus allows a user to control the percentage of grain size reduction by varying at least parameters, either individually or simultaneously. For example, a user can control the residence time of the grain-based fluid medium in the cavitation zone of the controlled flow cavitation apparatus. The residence time is influenced by the velocity of the grain-based fluid medium flowing through the apparatus, the diameter and length (l) of the orifice and the pressure ($P_2$) in the second chamber. A user can maintain the grain-based fluid medium in the cavitation zone for about 0.01 second to less than 0.001 second by controlling the velocity of the fluid medium. Another parameter under the control of the user is the processing pressure. For example, a user can vary the type and size of the pump used to pass the grain-based fluid medium through the controlled flow cavitation apparatus. The processing pressure can be adjusted and controlled to be in the range of 20 psi to 1000 psi. Lastly, a user can control the number of times the grain-based fluid medium is circulated through the controlled flow cavitation apparatus. The number of circulations can be unlimited, although a number between 1 and 100 is preferred. Appropriate adjustment of these parameters by a user can control the magnitude of grain size reduction (diameter) from less than 90 percent to as little as 5 percent of the original diameter of the grain in the grain-based liquid medium.

It should now be apparent that there has been provided, in accordance with the present invention, a novel process for reducing grain size in a grain-based liquid medium that satisfies the benefits and advantages set forth above. Moreover, it will be apparent to those skilled in the art that many modifications, variations, substitutions and equivalents for the features described above may be effected without departing from the spirit and scope of the invention. Accordingly, it is expressly intended that all such modifications, variations, substitutions and equivalents which fall within the spirit and scope of the invention as defined in the appended claims to be embraced thereby.

The preferred embodiments have been described, herein. It will be apparent to those skilled in the art that the above methods may incorporate changes and modifications without departing from the general scope of this invention. It is intended to include all such modifications and alterations in so far as they come within the scope of the appended claims or the equivalents thereof.

What is claimed is:

1. A method for producing alcohol from grain comprising: applying controlled flow cavitation to a liquid medium comprising a grain, wherein said controlled flow cavitation reduces the particle size of said grain.

2. The method of claim 1, wherein the average diameter of said grain in said liquid medium is reduced by at least 5 percent.

3. The method of claim 1, said controlled flow cavitation is applied to said liquid medium prior to distillation such that the average grain size in said liquid medium is reduced at least 5 percent.

4. The method of claim 1, said liquid medium being transferred through a pump to control the flow of said liquid medium.

5. The method of claim 4, said pump being selected from the group consisting of a centrifugal pump, a positive-displacement pump or a diaphragm pump.

6. The method of claim 4, said pump transferring said liquid medium at a processing pressure.

7. The method of claim 1, said applying controlled flow cavitation induces depolymerization of starch contained in said grain.

8. The method of claim 1, wherein said depolymerization of said starch increases the rate of liquefaction in said starch.

9. A method for increasing ethanol yield in a starch-to-ethanol production process comprising:
providing a grain-based liquid medium comprising grain and a liquid carrier; adjusting the processing pressure of said grain-based medium by passing said grain-based liquid medium through a pump;
applying controlled flow cavitation to said pressurized grain-based medium.

10. The method of claim 9, wherein the average diameter of said grain in said grain-based liquid medium is reduced by at least 5 percent.

* * * * *